United States Patent [19]

White

[11] 4,402,323

[45] Sep. 6, 1983

[54] DISPOSABLE ELECTROPHYSIOLOGICAL EXPLORING ELECTRODE NEEDLE

[75] Inventor: David L. White, Wyoming, Minn.

[73] Assignee: Medtronic, Inc., Minneapolis, Minn.

[21] Appl. No.: 262,882

[22] Filed: May 12, 1981

[51] Int. Cl.³ .......................... A61B 5/04; A61N 1/04
[52] U.S. Cl. .................................. 128/642; 128/785; 128/419 P
[58] Field of Search ............................... 128/784–786, 128/419 P, 642

[56] References Cited

U.S. PATENT DOCUMENTS

| 4,058,116 | 11/1977 | Bucclo | 128/784 X |
| 4,235,246 | 11/1980 | Weiss | 128/785 |
| 4,258,724 | 3/1981 | Balat et al. | 128/786 X |

OTHER PUBLICATIONS

"A Comparison of Left and Right Ventricular Pacing Using Medtronic Sutureless Lead", by Emil A. Naclerio, M.D. and Phillip Varriale, M.D., presented at the 26th American College of Cardiology in Las Vegas, Nev., Mar. 1977.

*Primary Examiner*—Lee S. Cohen
*Attorney, Agent, or Firm*—Reed A. Duthler; John L. Rooney; Joseph F. Breimayer

[57] ABSTRACT

Technique for permitting ease of mapping of the myocardial tissues during implantation of a myocardial electrode. The technique employs the use of a disposable exploring needle located on the distal end of the implantable lead assembly. The permanent electrode is attached to the exploring needle by being embedded into an electrically conducting material of the exploring needle. The implanting physician explores the electrical characteristics of the myocardial tissues using the exploring needle. Upon finding the desired electrode location, the exploring needle is removed and discarded and the electrode is permanently attached in the manner customary in the prior art.

8 Claims, 4 Drawing Figures

DISPOSABLE ELECTROPHYSIOLOGICAL EXPLORING ELECTRODE NEEDLE

BACKGROUND OF THE INVENTION

1. Field of the Invention

The present invention relates generally to implantable medical apparatus and, more specifically, relates to implantable electrodes and related apparatus.

2. Description of the Prior Art

The most popular electrode type for long-term attachment to the myocardial tissue is a structure having a helical electrode at its distal tip. This helical tip is screwed into the myocardium to establish chronic fixation and long-term electrical conductivity. Examples of such an electrode and insertion tools used in conjunction therewith may be found in U.S. Pat. No. 3,737,579 issued to Bolduc, U.S. Pat. No. 4,010,757 issued to Jula et al., and U.S. Pat. No. 4,207,903 issued to O'Neill, all assigned to the assignee of the present invention. These references teach the current state of the art relative to the insertion apparatus and techniques for implanting such chronic myocardial electrodes.

A problem with the techniques taught by the above-described references is in electrically mapping the myocardial surface. It is desirable during the implant procedure to find a location for installation of the electrode which provides optimal sensing and stimulation thresholds. The normal manner of doing this with the structures taught above is to press the helical electrode into contact with the epicardium and measure the sensed voltage. The disadvantage of this technique is that the helical electrode after chronic implantation will be screwed into the myocardium. Therefore, it will contact much different tissue than is contacted during the mapping procedure. The alternative of using this procedure is to screw the helical electrode into the myocardium to make mapping measurements. However this is considered far more traumatic to the myocardium then is justified.

A number of structures have been developed to enhance the mapping process. One such technique is taught by Barton et al. in U.S. Pat. No. 4,187,853. Barton et al. teach a probing needle 52 having a pointed distal end at 54 which is attached to the insertion tool. During the implantation procedure, point 54 of probe 52 is extended into the myocardium to make testing measurements. The probe is retracted into the lead body after the desired location has been found and the helical electrode permanently implanted using the standard procedure. This technique has as its major disadvantage, that the electrical path for conductivity during the mapping procedure does not involve the electrode to be chronically implanted. Therefore, the sensing and stimulation impedances observed during mapping will be substantially different from those to be experienced after chronic implantation.

An alternative technique is taught by Weiss in U.S. Pat. No. 4,235,246. As taught by Weiss, probing needle 38 is attached to the chronically implantable electrode. This techniques overcomes the problems found in the Barton et al method because it uses the electrically conductive path of the chronically implantable lead for mapping purposes. The Weiss technique, however, unduly complicates the chronically implantable electrode. That is to say, the retractable probing needle remains with the electrode after chronic implantation and, therefore, must itself be made highly biocompatible and must be of sufficient reliability not to contribute to the overall failure rate of the chronically implantable electrode.

The present invention uses a disposable exploring needle which uses the complete electrical path of the chronically implantable lead for the electrical mapping purposes, and yet does not impact the physical size or the characteristics of the electrode in its chronically implanted state.

SUMMARY OF THE INVENTION

The present invention uses a disposable easily detached electrical mapping needle in conjunction with an epicardial lead having a helical electrode. The helical electrode is screwed into the soft, but electrically conducting portion of the disposable exploring needle. A long pointed metallic probe extends distally from the assembly. Mapping is accomplished through the insertion of the long pointed probe tip into the myocardium and measuring the electrical characteristics through the electrical connector at the proximal end of the chronically implantable epicardial lead. Upon locating the optimal position for chronic implantation, the disposable exploring needle is removed and the helical electrode is inserted in the normal manner.

DETAILED DESCRIPTION OF THE PREFERRED EMBODIMENT

Preferred embodiments of the present invention are described in terms of their use with the Medtronic ® Model 6917 and Model 6917A Myocardial Leads. However, those of ordinary skill in the art will be able to apply this present invention to other related applications based on the disclosure found herein.

Figure 1:
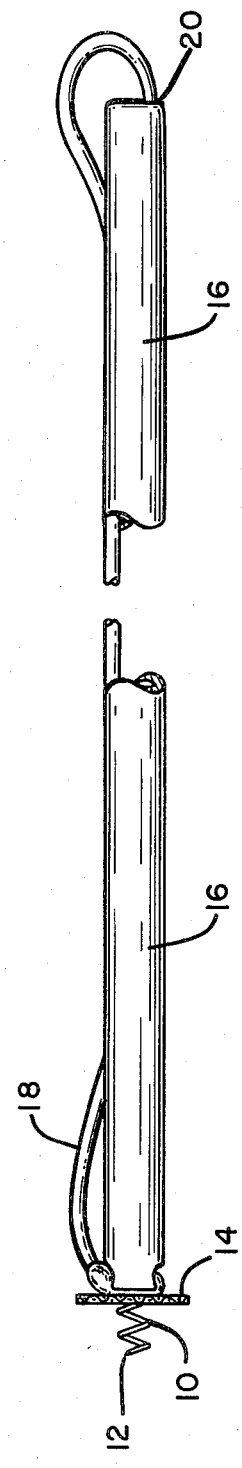
FIG. 1 is a prior art drawing of a chronically implantable myocardial lead assembly within its insertion tool.

FIG. 1 is a representation of a prior art myocardial pacing lead. It is shown as attached to insertion tool 16 in preparation for implantation. The insertion tool 16 is a generally elongated member having a tubular construction. The electrode body is frictionally engaged at the distal end of implantation tool 16. The main electrical conductor of the lead is designated reference 18. During implantation, this conductor is inserted into a slot of the body of insertion tool 16. The proximal end 20 of the myocardial lead having an electrical connector thereto is inserted into a slot in the proximal end of insertion tool 16. The distal end of the body implantable lead contains a surgical mesh 14 to assist in adding chronic stability. The electrode 10 is shown as a helix of metallic material which is screwed into the myocardium from pointed tip 12. For the reader desiring additional background into this prior art structure, reference is again made to U.S. Pat. Nos. 3,737,579; 4,010,757, and 4,207,903 mentioned above which are herein incorporated by reference.

Figure 2:
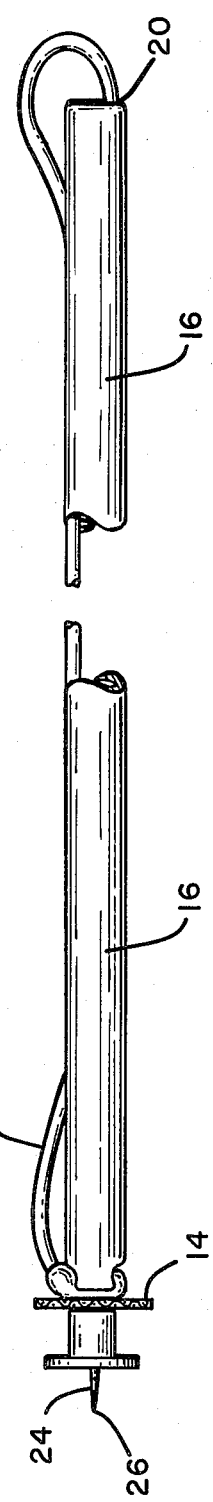
FIG. 2 is the same myocardial lead assembly as shown in FIG. 1 with the primary embodiment of the disposable exploration needle attached thereto.

FIG. 2 is a corresponding figure of an myocardial lead having a disposable exploratory needle attached thereto in accordance with the present invention. The helical electrode 10 (see also FIG. 1) cannot be seen in FIG. 2 as it is inserted into tubular member 22. The active mapping activity is accomplished using probing needle 24, which is of sufficient length to provide optimal probing depth. This optimal length should correspond to the depth within the myocardium to which helical electrode 10 will be positioned for chronic implantation. Probing needle 24 contains pointed tip 26, which is smoothly tapered for minimization of trauma to the myocardium. Probing needle 24 is preferably of metallic material such as stainless steel 304. Tubular member 22 is preferably of an insulating, body compatible material such as silicone rubber.

Figure 3:
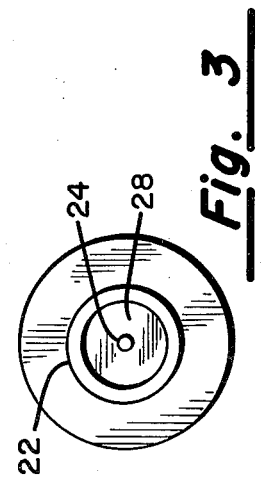
FIG. 3 is a view from the proximal end of the disposable exploring needle.

FIG. 3 is an end view of the disposable probing needle assembly. The view is taken from the proximal end looking toward the distal end. The tubular member 22 is shown. An auxiliary flange may also be used to insure that myocardial trauma is minimized. Material 28 is a soft material into which the electrode 10 may be screwed but which is also an electrical conductor. The normal technique for providing this capability is to use an electrically conducting silicone rubber which has been imbedded with conductive polymers or metallic particulates. Probing needle 24 extends through material 28 thereby sustaining electrical contact therewith.

Figure 4:
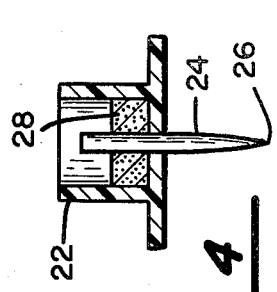
FIG. 4 is a side sectional view of the disposable exploring needle.

FIG. 4 is a side sectional view of the disposable probing needle assembly. Tubular member 22 is shown as containing material 28. As can be readily envisioned from this figure, electrode 10 is screwed into material 28 whereby electrical contact is sustained. This technique also insures that the entire disposable probe assembly is firmly anchored to the epicardial electrode. Probing needle 24 is shown as physically attached to tubular member 22 and also to material 28. In addition, electrical contact is thereby sustained between materials 28 and probing needle 24.

The present invention has been described in relationship to the two preferred embodiments herein. Those of ordinary skill in the art will be readily able to apply these teachings to other related applications.

What is claimed is:

1. A body implantable lead comprising:
    a conductor having a proximal end and a distal end;
    an insulating sheath covering said conductor;
    an electrical connector attached to said proximal end of said conductor;
    an electrode assembly suitable for chronic implantation, having a conductive fixation device electrically coupled to said distal end of said conductor; and
    means removably electrically coupled to said electrode assembly and removably frictionally engaged by said fixation device for establishing temporary electrical contact with body tissue.

2. A body implantable lead according to claim 1 wherein said fixation device is a conductive helical coil having a sharp distal tip for screwing into body tissue.

3. A body implantable lead according to claim 2 wherein said establishing means further comprises:
    a soft, conductive material into which said helical coil is screwed whereby said establishing means is electrically coupled to and frictionally engaged by said fixation device; and
    a probing needle mechanically attached to and electrically coupled to said soft conductive material.

4. A body implantable lead according to claim 3 wherein said establishing means further comprises:
    a tubular member housing said soft conductive material.

5. A body implantable lead according to claim 4 wherein said tubular member further comprises:
    an auxiliary flange to minimize tissue trauma.

6. A body implantable lead comprising:
    an insulated conductor having a proximal end and a distal end;
    an electrical connector electrically coupled to the proximal end of said insulated conductor;
    electrode means for insertion into body tissue electrically coupled to the distal end of said conductor; and
    means removably electrically and mechanically coupled to said electrode means for establishing temporary electrical contact with body tissue.

7. A body implantable lead according to claim 6 wherein said establishing means further comprises:
    a soft conductive material into which said electrode means is inserted to accomplish mechanical and electrical coupling; and
    a probing needle mechanically attached to and electrically coupled to said soft conductive material.

8. A body implantable lead according to claim 7 wherein said establishing means further comprises a tubular insulative member housing said soft conductive material.

* * * * *